United States Patent
Zhao et al.

(10) Patent No.: US 10,835,535 B2
(45) Date of Patent: Nov. 17, 2020

(54) CERTAIN PROTEIN KINASE INHIBITORS

(71) Applicants: Shanghai Fochon Pharmaceutical Co., Ltd., Shanghai (CN); Fochon Pharmaceuticals, Ltd., Nan'an District, Chongqing (CN)

(72) Inventors: Xingdong Zhao, Chongqing (CN); Tongshuang Li, Surrey (CA); Zhifang Chen, Chongqing (CN); Rui Tan, Chongqing (CN); Ling Chen, Chongqing (CN); Xianlong Wang, Chongqing (CN); Lijun Yang, Chongqing (CN); Zuwen Zhou, Chongqing (CN); Yanxin Liu, Chongqing (CN); Min Lin, Chongqing (CN); Jing Sun, Chongqing (CN); Weibo Wang, Moraga, CA (US)

(73) Assignees: Shanghai Fochon Pharmaceutical Co., Ltd., Shanghai (CN); Fochon Pharmaceuticals, Ltd., Chongqing (CN)

( * ) Notice: Subject to any disclaimer, the term of this patent is extended or adjusted under 35 U.S.C. 154(b) by 0 days.

(21) Appl. No.: 16/099,218

(22) PCT Filed: May 5, 2017

(86) PCT No.: PCT/CN2017/083162
§ 371 (c)(1),
(2) Date: Nov. 6, 2018

(87) PCT Pub. No.: WO2017/193872
PCT Pub. Date: Nov. 16, 2017

(65) Prior Publication Data
US 2019/0209566 A1    Jul. 11, 2019

Related U.S. Application Data

(60) Provisional application No. 62/333,165, filed on May 7, 2016.

(51) Int. Cl.
  *A61K 31/519*   (2006.01)
  *C07D 495/04*   (2006.01)
  *A61K 31/5377*  (2006.01)
  *A61K 45/06*    (2006.01)

(52) U.S. Cl.
  CPC ........ *A61K 31/519* (2013.01); *A61K 31/5377* (2013.01); *A61K 45/06* (2013.01); *C07D 495/04* (2013.01)

(58) Field of Classification Search
  CPC ............................ A61K 31/519; C07D 495/04
  See application file for complete search history.

(56) References Cited

FOREIGN PATENT DOCUMENTS

WO    2009062258    5/2009
WO    2015180642    12/2015

OTHER PUBLICATIONS

Wang et al., 2015, caplus an 2015:1932849.*
Restenosis, 2020, https://www.healthline.com/health/restenosis#diagnosis.*
CancerPrevention, 2020, https://www.preventcancer.org/education/preventable-cancers/.*
Psoriasis, 2020, https://www.mayoclinic.org/diseases-conditions/psoriasis/diagnosis-treatment/drc-20355845.*
Carry et al., 2013, caplus an 2013:1555370.*
Int'l Search Report dated Jul. 18, 2017 in Int'l Application No. PCT/CN2017/083162.

* cited by examiner

*Primary Examiner* — Sun Jae Yoo
(74) *Attorney, Agent, or Firm* — Ice Miller LLP

(57) ABSTRACT

Certain CDK4/6 inhibitors and pharmaceutically acceptable salts thereof are described. In particular, these compounds can inhibit kinase activity of CDK4/6 and may be useful for the treatment of hyper-proliferative diseases like cancer and inflammation. In addition, the pharmaceutical compositions thereof and methods of use thereof are also described.

17 Claims, No Drawings

CERTAIN PROTEIN KINASE INHIBITORS

CROSS-REFERENCE TO RELATED APPLICATIONS

This application is a Section 371 of International Application No. PCT/CN2017/083162, filed May 5, 2017, which was published in the English language on Nov. 16, 2017 under International Publication No. WO 2017/193872 A1, which claims the benefit of U.S. provisional application No. 62/333,165, filed May 7, 2016, the disclosures of which are incorporated herein by reference in their entireties.

FIELD OF THE INVENTION

Provided are certain compounds or pharmaceutically acceptable salts thereof which can inhibit kinase activity of CDK4/6 and may be useful for the treatment of hyper-proliferative diseases like cancer and inflammation.

BACKGROUND OF THE INVENTION

Hyper-proliferative diseases like cancer and inflammation are attracting the scientific community to provide therapeutic benefits. In this regard efforts have been made to identify and target specific mechanisms which play a role in proliferating the diseases.

Tumor development is closely associated with genetic alteration and deregulation of cyclin-dependent kinases (CDKs) and their regulators, suggesting that inhibitors of CDKs may be useful anti-cancer therapeutics.

CDKs are serine/threonine protein kinases, which are the driving force behind the cell cycle and cell proliferation. CDKs regulate initiation, progression, and completion of mammalian cell cycle, and they are critical for cell growth. Most of the known CDK's, including CDK1 through CDK9, are involved either directly or indirectly in cell cycle progression. Those directly involved with cell cycle progression, such as CDK1-4 and 6, can be classified as G1, S, or G2M phase enzymes. Uncontrolled proliferation is a hallmark of cancer cells and the alteration of CDK function occurs with high frequency in many solid tumors.

The pivotal roles of CDKs, and their associated proteins, in coordinating and driving the cell cycle in proliferating cells have been outlined. The development of monotherapies for the treatment of proliferative disorders, such as cancers, using therapeutics targeted generically at CDKs, or at specific CDKs, is therefore potentially highly desirable. CDK inhibitors could conceivably also be used to treat other conditions such as viral infections, autoimmune diseases and neuro-degenerative diseases, amongst others. CDKs targeted therapeutics may also provide clinical benefits in the treatment of the previously described diseases when used in combination therapy with either existing, or new, therapeutic agents.

Therefore, a compound having an inhibitory activity on CDK will be useful for the prevention or treatment of cancer. Although CDK4/6 inhibitors were disclosed in the arts, e.g., WO2010020675 and WO2012064805, many suffer from having short half-life or toxicity. Therefore, there is a need for new CDK4/6 inhibitors that have at least one advantageous property selected from potency, stability, selectivity, toxicity, pharmacodynamic and pharmacokinetic properties as an alternative for the treatment of hyper-proliferative diseases. In this regard, a novel class of CDK4/6 inhibitors is provided herein.

DISCLOSURE OF THE INVENTION

Disclosed herein are certain novel 6-5 membered fused ring derivatives and pharmaceutical compositions thereof, and their use as pharmaceuticals.

In one aspect, disclosed herein is a compound of formula (I):

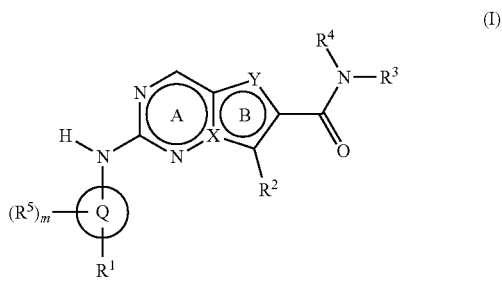

or a pharmaceutically acceptable salt thereof, wherein
X is C or N;
Y is $CR^{11}$, O, S or $NR^{12}$;
6-5 membered fused ring system A-B is selected from

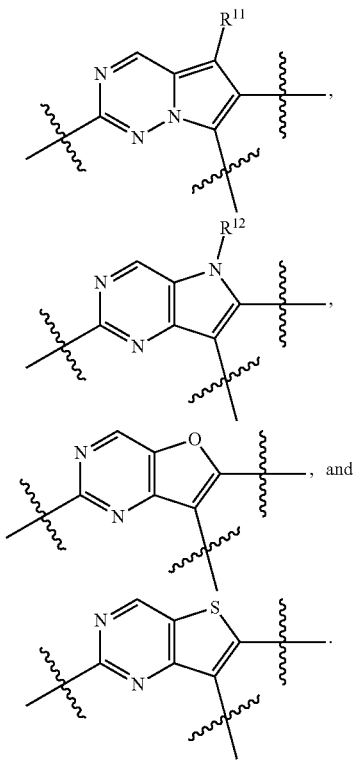

Q is selected from aryl and heteroaryl;
$R^1$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;

$R^2$ is selected from hydrogen, halogen, hydroxyl, CN, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

$R^3$ and $R^4$ are independently selected from hydrogen, $C_{1-10}$ alkyl, $C_{2-10}$ alkenyl, $C_{2-10}$ alkynyl, and $C_{3-10}$ cycloalkyl; wherein alkyl, alkenyl, alkynyl, and cycloalkyl are each unsubstituted or substituted with at least one substituent, such as one, two, three, or four substituents, independently selected from $R^{6a}$; or $R^3$ and $R^4$ together with the nitrogen atoms to which they are attached form a 4-12 membered ring containing, 1, 2 or 3 heteroatoms independently selected from oxygen, sulfur and nitrogen, and optionally substituted with 1 or 2 $R^{6a}$ groups;

with the proviso that when $R^3$ and $R^4$ are both hydrogen, $R^2$ is not aryl or heteroaryl;

each $R^5$ is independently selected from hydrogen, $C_{1-10}$ alkyl, $C_{2-10}$ alkenyl, $C_{2-10}$ alkynyl, $C_{3-10}$ cycloalkyl, —$OR^8$, —$NR^7S(O)_rR^8$, —$NO_2$, halogen, —$S(O)_rR^7$, —$SR^8$, —$S(O)_2OR^7$, —$OS(O)_2R^8$, —$S(O)_rNR^7R^8$, —$NR^7R^8$, —$O(CR^9R^{10})_tNR^7R^8$, —$C(O)R^7$, —$CO_2R^8$, —$CO_2(CR^9R^{10})_tCONR^7R^8$, —$OC(O)R^7$, —CN, —$C(O)NR^7R^8$, —$NR^7C(O)R^8$, —$OC(O)NR^7R^8$, —$NR^7C(O)OR$, —$NR^7C(O)NR^7R^8$, —$CR^7(N—OR^8)$, —$CHF_2$, —$CF_3$, —$OCHF_2$, and —$OCF_3$; wherein $C_{10}$ alkyl, $C_{2-10}$ alkenyl, $C_{2-10}$ alkynyl, and $C_{3-10}$ cycloalkyl are each unsubstituted or substituted with at least one substituent, such as one, two, three, or four substituents, independently selected from $R^{6a}$;

each $R^{6a}$ is independently selected from $C_{1-10}$ alkyl, $C_{2-10}$ alkenyl, $C_{2-10}$ alkynyl, $C_{3-10}$ cycloalkyl, heterocyclyl, heterocyclyl-$C_{1-4}$ alkyl, —$OR^8$, —$NR^7S(O)_rR^8$, —$NO_2$, -halogen, —$S(O)_rR^7$, —$SR^8$, —$S(O)_2OR^7$, —$OS(O)_2R^8$, —$S(O)_rNR^7R^8$, —$NR^7R^8$, —$(CR^9R^{10})_tOR^8$, —$(CR^9R^{10})_tNR^7R^8$, —$(CR^9R^{10})_tSR^8$, —$(CR^9R^{10})_tS(O)_rR^8$, —$(CR^9R^{10})_tCO_2R^8$, —$(CR^9R^{10})_tCONR^7R^8$, —$(CR^9R^{10})_tNR^7CO_2R^8$, —$(CR^9R^{10})_tOCONR^7R^8$, —$(CR^9R^{10})_tNR^7CONR^7R^8$, —$(CR^9R^{10})_tNR^7SO_2NR^7R^8$, —$O(CR^9R^{10})_tNR^7R^8$, —$C(O)R^7$, —$C(O)(CR^9R^{10})_tOR^8$, —$C(O)(CR^9R^{10})_tNR^7R^8$, —$C(O)(CR^9R^{10})_tSR^8$, —$C(O)(CR^9R^{10})_tS(O)_rR^8$, —$CO_2R^8$, —$CO_2(CR^9R^{10})_tCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CR^7(N—OR^8)$, —$CHF_2$, —$CF_3$, —$OCHF_2$ and —$OCF_3$;

each $R^{6b}$ is independently selected from $R^{6a}$, aryl, aryl-$C_{1-4}$ alkyl, heteroaryl, and heteroaryl-$C_{1-4}$ alkyl;

each $R^7$ and each $R^8$ are independently selected from hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; wherein alkyl, alkenyl, alkynyl, cycloalkyl, and heterocyclyl are each unsubstituted or substituted with at least one substituent, such as one, two, three, or four substituents, independently selected from $R^{6a}$, and aryl and heteroaryl are each unsubstituted or substituted with at least one substituent, such as one, two, three, or four substituents, independently selected from $R^{6b}$; or $R^7$ and $R^8$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 $R^{6b}$ groups;

each $R^9$ and each $R^{10}$ are independently selected from hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; or $R^9$ and $R^{10}$ together with the carbon atom(s) to which they are attached form a ring of 3 to 7 members containing 0, 1, or 2 heteroatoms independently selected from oxygen, sulfur and nitrogen, and optionally substituted with 1 or 2 $R^{6a}$ groups;

$R^{11}$ is selected from hydrogen, $C_{1-10}$ alkyl, $C_{3-10}$ cycloalkyl, $C_{3-10}$ cycloalkylalkyl, heterocyclyl, heterocyclylalkyl, aryl, aryl-$C_{1-4}$ alkyl, heteroaryl, heteroaryl-$C_{1-4}$ alkyl, —$OR^7$, —$NR^7S(O)_rR^8$, —$S(O)_rR^7$, —$SR^7$, —$S(O)_2OR^7$, —$OS(O)_2R^7$, —$S(O)_rNR^7R^8$, —$NR^7R^8$, —$O(CR^9R^{10})_tNR^7R^8$, —$C(O)R^7$, —$CO_2R^8$, —$CO_2(CR^9R^{10})_tCONR^7R^8$, —$OC(O)R^7$, —CN, —$C(O)NR^7R^8$, —$NR^7C(O)R^8$, —$OC(O)NR^7R^8$, —$NR^7C(O)OR^8$, —$NR^7C(O)NR^7R^8$, —$CHF_2$, —$CF_3$, —$OCHF_2$, and —$OCF_3$;

$R^{12}$ is selected from hydrogen, $C_{1-10}$ alkyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —$S(O)_rR^7$, —$C(O)R^7$, —$CO_2R^7$, —$CO_2(CR^9R^{10})_tCONR^7R^8$, and —$C(O)NR^7R^8$;

m is independently selected from 0, 1, 2, and 3;

each r is independently selected from 1 and 2;

each t is independently selected from 1, 2, and 3.

In some embodiments, disclosed herein is a compound of formula (II):

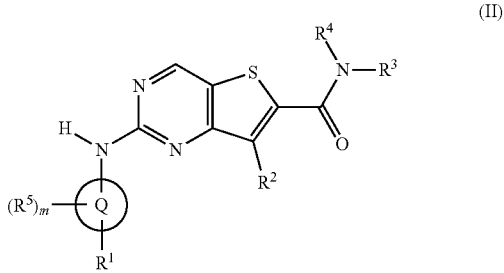

or a pharmaceutically acceptable salt thereof, wherein:

Q is heteroaryl;

$R^1$ is heterocycle which is unsubstituted or substituted with at least one substituent, such as one, two, three, or four substituents, independently selected from $R^X$;

$R^2$ is $C_{3-10}$ cycloalkyl;

$R^3$ is selected from hydrogen, $C_{1-6}$ alkyl and $C_{3-10}$ cycloalkyl;

$R^4$ is selected from hydrogen, $C_{1-6}$ alkyl and $C_{3-10}$ cycloalkyl;

$R^5$ is independently selected from hydrogen and halogen;

each $R^X$ is independently selected from heterocyclyl, which is unsubstituted or substituted with at least one substituent, such as one, two, three, or four substituents, independently selected from $R^Y$;

each $R^Y$ is independently selected from halogen, OH, CN, amino, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$ alkoxyalkyl, $C_{3-10}$ cycloalkoxy, $C_{1-6}$ alkylthio, $C_{3-10}$ cycloalkylthio, $C_{1-6}$ alkylamino, $C_{3-10}$ cycloalkylamino, di($C_{1-6}$ alkyl)amino;

m is selected from 0, 1, 2 and 3.

In some embodiments, Q is pyridinyl.

In some embodiments, Q is

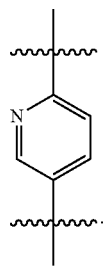

In some embodiments, $R^1$ is selected from piperazinyl and piperidinyl.
In some embodiments, $R^1$ is piperazinyl.
In some embodiments, $R^2$ is selected from cyclopentyl and cyclohexyl.
In some embodiments, $R^2$ is cyclopentyl.
In some embodiments, $R^3$ is $C_{1-6}$ alkyl.
In some embodiments, $R^3$ is methyl.
In some embodiments, $R^4$ is $C_{1-6}$ alkyl.
In some embodiments, $R^4$ is methyl.
In some embodiments, $R^5$ is hydrogen.
In some embodiments, $R^X$ is selected from piperazinyl and piperidinyl.
In some embodiments, $R^Y$ is $C_{1-6}$ alkyl.
In some embodiments, $R^Y$ is selected from methyl and ethyl.
In some embodiments, m is selected from 0 and 1.
In some embodiments, m is 0.
Also provided is a compound, selected from
7-cyclopentyl-N,N-dimethyl-2-((5-(4-(piperidin-4-yl)piperazin-1-yl)pyridin-2-yl)amino)thieno[3,2-d]pyrimidine-6-carboxamide,
7-cyclopentyl-2-((5-(4-(1-ethylpiperidin-4-yl)piperazin-1-yl)pyridin-2-yl)amino)-N,N-dimethylthieno[3,2-d]pyrimidine-6-carboxamide,
7-cyclopentyl-N,N-dimethyl-2-((5-(4-(1-methylpiperidin-4-yl)piperazin-1-yl)pyridin-2-yl)amino)thieno[3,2-d]pyrimidine-6-carboxamide,
7-cyclopentyl-N,N-dimethyl-2-((5-(4-(piperazin-1-yl)piperidin-1-yl)pyridin-2-yl)amino)thieno[3,2-d]pyrimidine-6-carboxamide,
7-cyclopentyl-N,N-dimethyl-2-((5-(4-(4-methylpiperazin-1-yl)piperidin-1-yl)pyridin-2-yl)amino)thieno[3,2-d]pyrimidine-6-carboxamide,
7-cyclopentyl-2-((5-(4-(4-ethylpiperazin-1-yl)piperidin-1-yl)pyridin-2-yl)amino)-N,N-dimethylthieno[3,2-d]pyrimidine-6-carboxamide,
7-cyclopentyl-N,N-dimethyl-2-((5-(4-morpholinopiperidin-1-yl)pyridin-2-yl)amino)thieno[3,2-d]pyrimidine-6-carboxamide,
and pharmaceutically acceptable salts thereof.

In yet another aspect, the present disclosure provides a pharmaceutical composition comprising a compound of formula (II) or a pharmaceutically acceptable salt thereof and a pharmaceutically acceptable excipient.

In yet another aspect, the disclosure provides a method for modulating CDK4/6, comprising administering to a system or a subject in need thereof, a therapeutically effective amount of a compound of formula (II) or a pharmaceutically acceptable salt thereof or pharmaceutical compositions thereof, thereby modulating said CDK4/6.

In yet another aspect, disclosed is a method to treat, ameliorate or prevent a condition which responds to inhibition of CDK4/6 comprising administering to a system or subject in need of such treatment an effective amount of a compound of formula (II) or a pharmaceutically acceptable salt thereof or pharmaceutical compositions thereof, and optionally in combination with a second therapeutic agent, thereby treating said condition.

Alternatively, the present disclosure provides the use of a compound of formula (II) or a pharmaceutically acceptable salt thereof in the manufacture of a medicament for treating a condition mediated by CDK4/6. In particular embodiments, the compounds of the disclosure may be used alone or in combination with a second therapeutic agent to treat a condition mediated by CDK4/6.

Alternatively, disclosed is a compound of formula (II) for treating a condition mediated by CDK4/6.

Specifically, the condition herein includes but not limited to, an autoimmune disease, a transplantation disease, an infectious disease or a cell proliferative disorder.

Furthermore, the disclosure provides a method for treating a cell proliferative disorder, comprising administering to a system or subject in need of such treatment an effective amount of a compound of formula (II) or a pharmaceutically acceptable salt thereof or a pharmaceutical composition thereof, and optionally in combination with a second therapeutic agent, thereby treating said condition.

Alternatively, the present disclosure provides the use of a compound of formula (II) or a pharmaceutically acceptable salt thereof in the manufacture of a medicament for treating a cell-proliferative disorder. In particular examples, the compound of the disclosure may be used alone or in combination with a chemotherapeutic agent to treat a cell proliferative disorder.

Specifically, the cell proliferative disorder disclosed herein includes but not limited to, lymphoma, osteosarcoma, melanoma, or a tumor of breast, renal, prostate, colorectal, thyroid, ovarian, pancreatic, neuronal, lung, uterine or gastrointestinal tumor.

In the above method for using the compounds of the disclosure, a compound of formula (II) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, CH$_2$O is equivalent to OCH$_2$.

The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "hydrogen" refers to $^1$H, $^2$H and $^3$H.

The term "alkyl", employed alone or in combination with other terms, refers to both branched and straight-chain saturated aliphatic hydrocarbon groups having the specified number of carbon atoms. Unless otherwise specified, "alkyl" refers to $C_{1-10}$ alkyl. For example, $C_{1-6}$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane, and tricyclo[3.3.1.1$^{3,7}$]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terms, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH (alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
- 5- to 8-membered aromatic, monocyclic rings containing one or more, for example, from 1 to 4, or, in some embodiments, from 1 to 3, heteroatoms selected from N, O, and S, with the remaining ring atoms being carbon;
- 8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and
- 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, and nitrogen, as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, and nitrogen. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, 1,4-piperazinyl, and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, for example:

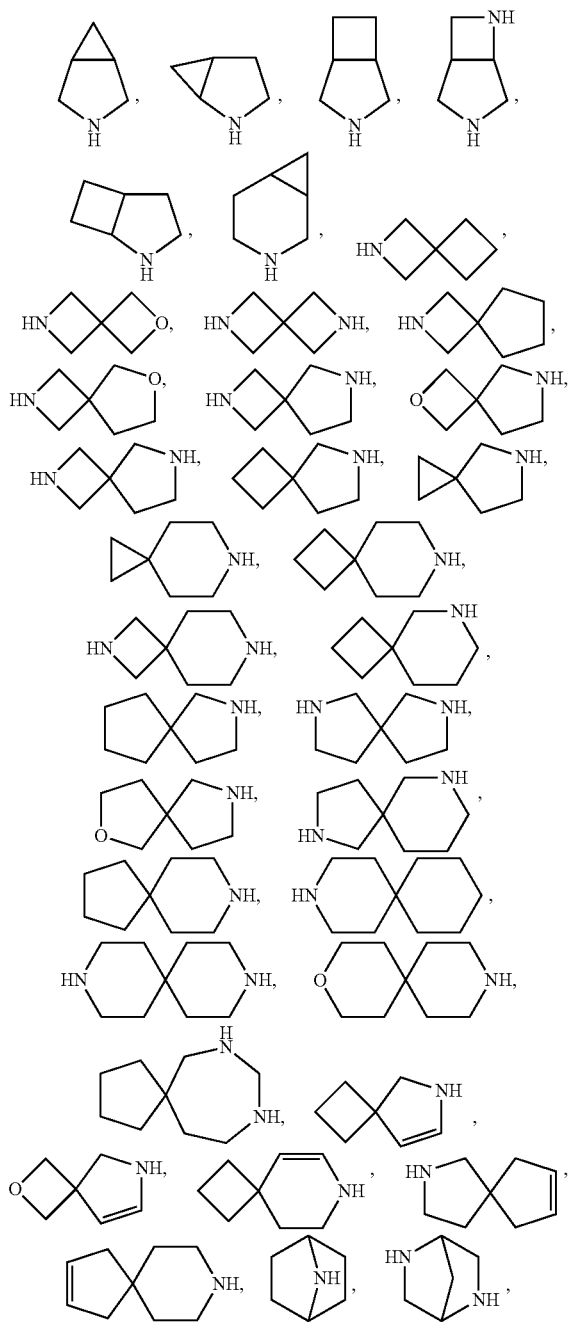

-continued

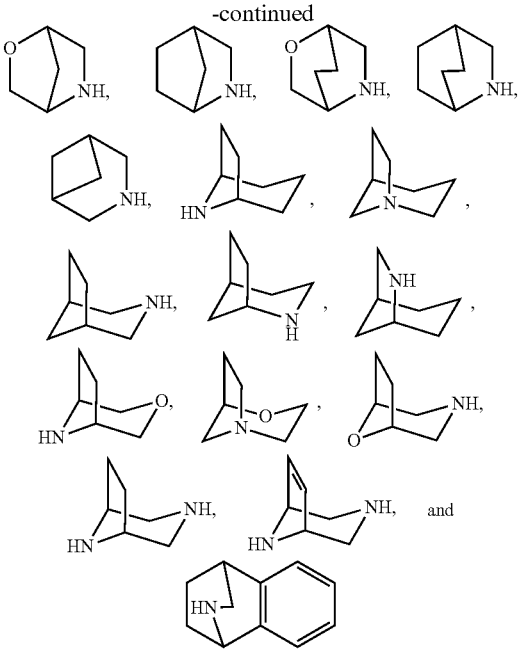

As used herein, "aryl-alkyl" refers to an alkyl moiety substituted by an aryl group. Example aryl-alkyl groups include benzyl, phenethyl, and naphthylmethyl groups. In some embodiments, aryl-alkyl groups have from 7 to 20 or 7 to 11 carbon atoms. When used in the phrase "aryl-$C_{1-4}$ alkyl", the term "$C_{1-4}$" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$ alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$ alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituents, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. "Prophylaxis" refers to preventing additional symptoms and preventing the underlying metabolic causes of symptoms, and includes achieving a prophylactic benefit. For prophylactic benefit, the compositions may be administered to a patient at risk of developing a particular disease, or to a patient reporting one or more of the physiological symptoms of a disease, even though a diagnosis of this disease may not have been made.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyloxycarbonyl, 4-(phenylazo)-benzyloxycarbonyl, 2-furfuryloxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl) methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl) ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group" as used herein includes, but not limited to, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl) ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Fut, 21(11), 1116 (1996); Brickner, S J et al., J Med Chem, 39(3), 673 (1996); Mallesham, B et al, Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK4/6 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999).

In addition, non-radio active isotope containing drugs, such as deuterated drugs called "heavy drugs" can be used for the treatment of diseases and conditions related to CDK4/6 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an Embodiment (1), this invention provides a compound of formula (II):

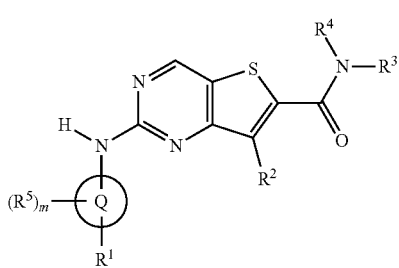

(II)

or a pharmaceutically acceptable salt thereof, wherein

Q is heteroaryl;

$R^1$ is heterocycle which is substituted with at least one substituent, such as one, two, three, or four substituents, independently selected from $R^X$;

$R^2$ is $C_{3-10}$ cycloalkyl;

$R^3$ is selected from hydrogen, $C_{1-6}$ alkyl and $C_{3-10}$ cycloalkyl;

$R^4$ is selected from hydrogen, $C_{1-6}$ alkyl and $C_{3-10}$ cycloalkyl;

$R^5$ is independently selected from hydrogen and halogen;

each $R^X$ is independently selected from heterocyclyl, which is unsubstituted or substituted with at least one substituent, such as one, two, three, or four substituents, independently selected from $R^Y$;

each $R^Y$ is independently selected from halogen, OH, CN, amino, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$ alkoxyalkyl, $C_{3-10}$ cycloalkoxy, $C_{1-6}$ alkylthio, $C_{3-10}$ cycloalkylthio, $C_{1-6}$ alkylamino, $C_{3-10}$ cycloalkylamino, di($C_{1-6}$ alkyl)amino;

m is selected from 0, 1, 2 and 3.

In another Embodiment (2), the invention provides a compound of Embodiment (1) or a pharmaceutically acceptable salt thereof, wherein Q is pyridinyl.

In another Embodiment (3), the invention provides a compound of Embodiment (2) or a pharmaceutically acceptable salt thereof, wherein Q is

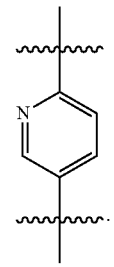 [SMILES: *c1ccc(*)nc1]

In another Embodiment (4), the invention provides a compound of any one of Embodiments (1)-(3) or a pharmaceutically acceptable salt thereof, wherein $R^1$ is selected from piperazinyl and piperidinyl, which are independently substituted with at least one substituent independently selected from $R^X$.

In another Embodiment (5), the invention provides a compound of Embodiment (5) or a pharmaceutically acceptable salt thereof, wherein each $R^X$ is independently selected from piperazinyl, piperidinyl and morpholinyl, which is unsubstituted or substituted with at least one substituent independently selected from $R^Y$.

In another Embodiment (6), the invention provides a compound of Embodiment (5) or a pharmaceutically acceptable salt thereof, wherein each $R^Y$ is independently selected from $C_{1-6}$ alkyl.

In another Embodiment (7), the invention provides a compound of Embodiment (6) or a pharmaceutically acceptable salt thereof, wherein $R^Y$ is selected from methyl and ethyl.

In another Embodiment (8), the invention provides a compound of any one of Embodiments (1)-(7) or a pharmaceutically acceptable salt thereof, wherein $R^2$ is selected from cyclopentyl and cyclohexyl.

In another Embodiment (9), the invention provides a compound of Embodiment (8) or a pharmaceutically acceptable salt thereof, wherein $R^2$ is cyclopentyl.

In another Embodiment (10), the invention provides a compound of any one of Embodiments (1)-(9) or a pharmaceutically acceptable salt thereof, wherein $R^3$ and $R^4$ are independently hydrogen or $C_{1-6}$ alkyl.

In another Embodiment (11), the invention provides a compound of Embodiment (10) or a pharmaceutically acceptable salt thereof, wherein $R^3$ and $R^4$ are independently methyl.

In another Embodiment (12), the invention provides a compound of any one of Embodiments (1)-(11) or a pharmaceutically acceptable salt thereof, wherein $R^5$ is hydrogen.

In another Embodiment (13), the invention provides a compound selected from 7-cyclopentyl-N,N-dimethyl-2-((5-(4-(piperidin-4-yl)piperazin-1-yl)pyridin-2-yl)amino)thieno[3,2-d]pyrimidine-6-carboxamide, 7-cyclopentyl-2-((5-(4-(1-ethylpiperidin-4-yl)piperazin-1-yl)pyridin-2-yl)amino)-N,N-dimethylthieno[3,2-d]pyrimidine-6-carboxamide, 7-cyclopentyl-N,N-dimethyl-2-((5-(4-(1-methylpiperidin-4-yl)piperazin-1-yl)pyridin-2-yl)amino)thieno[3,2-d]pyrimidine-6-carboxamide, 7-cyclopentyl-N,N-dimethyl-2-((5-(4-(piperazin-1-yl)piperidin-1-yl)pyridin-2-yl)amino)thieno[3,2-d]pyrimidine-6-carboxamide, 7-cyclopentyl-N,N-dimethyl-2-((5-(4-(4-methylpiperazin-1-yl)piperidin-1-yl)pyridin-2-yl)amino)thieno[3,2-d]pyrimidine-6-carboxamide, 7-cyclopentyl-2-((5-(4-(4-ethylpiperazin-1-yl)piperidin-1-yl)pyridin-2-yl)amino)-N,N-dimethylthieno[3,2-d]pyrimidine-6-carboxamide, 7-cyclopentyl-N,N-dimethyl-2-((5-(4-morpholinopiperidin-1-yl)pyridin-2-yl)amino)thieno[3,2-d]pyrimidine-6-carboxamide, 7-cyclopentyl-N,N-dimethyl-2-((5-(4-(4-(methyl-$d_3$)piperazin-1-yl)piperidin-1-yl)pyridin-2-yl)amino)thieno[3,2-d]pyrimidine-6-carboxamide, and pharmaceutically acceptable salts thereof.

In another Embodiment (14), the invention provides a pharmaceutical composition comprising a compound of any one of Embodiments (1) to (13) or a pharmaceutically acceptable salts thereof and at least one pharmaceutically acceptable carrier.

In another Embodiment (15), the invention provides a method of treating, ameliorating or preventing a condition, which responds to inhibition of cyclin-dependent kinase 4/6, comprising administering to a subject in need of such treatment an effective amount of a compound of any one of Embodiments (1) to (13), or a pharmaceutically acceptable salt thereof, or a pharmaceutical composition thereof, and optionally in combination with a second therapeutic agent.

In another Embodiment (16), the invention provides a use of a compound of any one of Embodiments (1) to (13) or a pharmaceutically acceptable salt thereof in the preparation of a medicament for treating a cell-proliferative disorder.

In yet another of its aspects, there is provided a kit comprising a compound disclosed herein, or a pharmaceutically acceptable salts thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salts thereof.

In another of its aspects, there is provided a method of inhibiting a CDK4/6 kinase comprising contacting the CDK4/6 with a compound disclosed herein, or a pharmaceutically acceptable salts thereof.

In yet another of its aspects, there is provided a method of inhibiting a CDK4/6 comprising causing a compound disclosed herein, or a pharmaceutically acceptable salts thereof to be present in a subject in order to inhibit the CDK4/6 in vivo.

In a further of its aspects, there is provided a method of inhibiting CDK4/6 comprising administering a first compound to a subject that is converted in vivo to a second compound wherein the second compound inhibits the CDK4/6 in vivo, the second compound being a compound according to any one of the above embodiments and variations.

In another of its aspects, there is provided a method of treating a disease state for which a CDK4/6 possesses activity that contributes to the pathology and/or symptomology of the disease state, the method comprising causing a compound disclosed herein, or a pharmaceutically acceptable salts thereof to be present in a subject in a therapeutically effective amount for the disease state.

In a further of its aspects, there is provided a method of treating a disease state for which a CDK4/6 possesses activity that contributes to the pathology and/or symptomology of the disease state, the method comprising administering a first compound to a subject that is converted in vivo to a second compound wherein the second compound inhibits the CDK4/6 in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the CDK4/6 gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting a CDK4/6.

In a further of its aspects, the present invention relates to the use of a compound according to any one of the above embodiments and variations in the manufacture of a medicament for treating a disease state for which a CDK4/6 possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid.

The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

EXAMPLES

Various methods may be developed for synthesizing a compound of formula (II) or a pharmaceutically acceptable salt thereof. Representative methods for synthesizing a compound of formula (II) or a pharmaceutically acceptable salt thereof are provided in the Examples. It is noted, however, that a compound of formula (II) or a pharmaceutically acceptable salt thereof may also be synthesized by other synthetic routes that others may devise.

It will be readily recognized that certain compounds of formula (II) have atoms with linkages to other atoms that confer a particular stereochemistry to the compound (e.g., chiral centers). It is recognized that synthesis of a compound of formula (II) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (II) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (II) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (II) are set forth in the definitions section of this Application. Alternatively, the salt forms of the compounds of formula (I) can be prepared using salts of the starting materials or intermediates.

The free acid or free base forms of the compounds of formula (II) can be prepared from the corresponding base addition salt or acid addition salt form. For example, a compound of formula (II) in an acid addition salt form can be converted to the corresponding free base thereof by treating with a suitable base (e.g., ammonium hydroxide solution, sodium hydroxide, and the like). A compound of formula (II) in a base addition salt form can be converted to the corresponding free acid thereof by, for example, treating with a suitable acid (e.g., hydrochloric acid, etc).

The N-oxides of a compound of formula (II) or a pharmaceutically acceptable salt thereof can be prepared by methods known to those of ordinary skill in the art. For example, N-oxides can be prepared by treating an unoxidized form of the compound of formula (II) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (II) can be prepared from the N-oxide of an appropriate starting material.

Compounds of formula (II) in an unoxidized form can be prepared from N-oxides of compounds of formula (II) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (II) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); pL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

A compound of formula II or a pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present invention are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration of the synthesis of the compounds of formula II, one of the synthetic approaches is outlined in Scheme 1. As shown in Scheme 1, the compounds of formula II can be assembled from intermediates III and IV, which are either known in the literature or prepared by methods familiar to those skilled in the art. Coupling of pyrimidinyl derivatives of formula III with amino-arene compounds of formula IV under conditions such as Buchwald-Hartwig amination or other amination conditions known in the literature leads to compounds of formula II.

Scheme 1

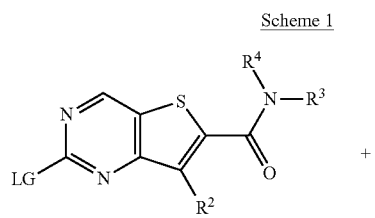

III
LG = Leaving Group

+

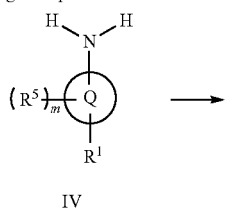

IV

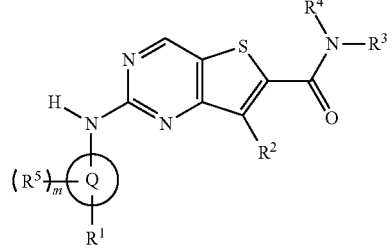

II

As an illustration of the preparation of intermediates of formula III, one synthetic route of IIIa is shown in Scheme 2. Starting from pyrimidinyl-substituted carboxylic acid IIa-a, intermediate IIa-c is prepared by decarboxylative coupling of IIa-a with aldehyde IIIa-b. Oxidation of the hydroxyl group in IIa-c leads to ketone IIIa-d which can be transformed into thienopyrimidine IIIa-e via a sequence of nucleophilic displacement of the bromide in intermediate IIa-d and in-situ intramolecular cyclization reaction. Manipulation of the ester group in IIIa-e into an amide group provides IIIa-g. Oxidation of IIIa-g with an oxidant such as mCPBA results in intermediates of formula IIIa.

Scheme 2

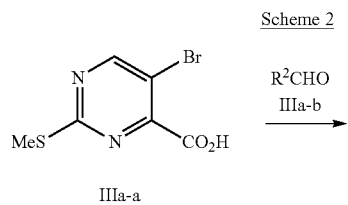

IIIa-a

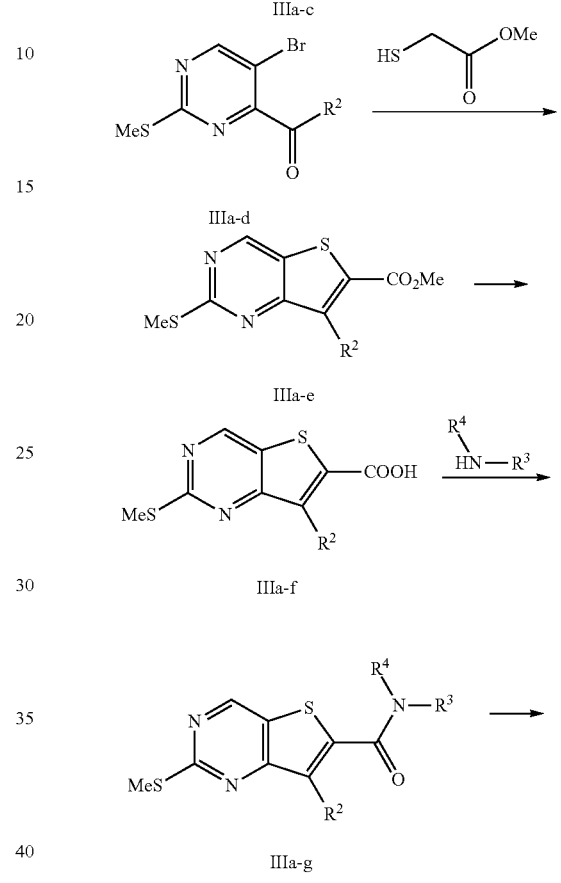

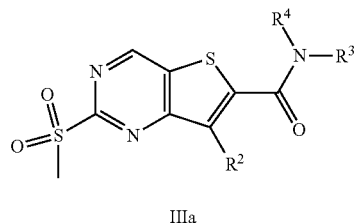

IIIa

As a further illustration of the preparation of intermediates of formula III, a preparation of compound of formula IIIb is provided in Scheme 3. Reaction of the amino thiophene IIIb-a with reagents such as chlorosulfonyl isocyanate (CSI) followed by hydrolysis under acidic conditions gives urea IIIb-c. Treatment of IIIb-c with a base such as sodium ethoxide in protic solvents such as ethanol leads to thienopyrimdine IIIb-d. Conversion of the hydroxyl groups in IIIb-d into chlorides provides IIIb-e. Selective removal of the chloride at C-4 pyrimidine in IIIb-e under conditions such as Pd/C/H$_2$ gives intermediate IIIb-f. Conversion of the ester group in IIIb-f into amide group finally gives intermediate IIIb.

Scheme 3

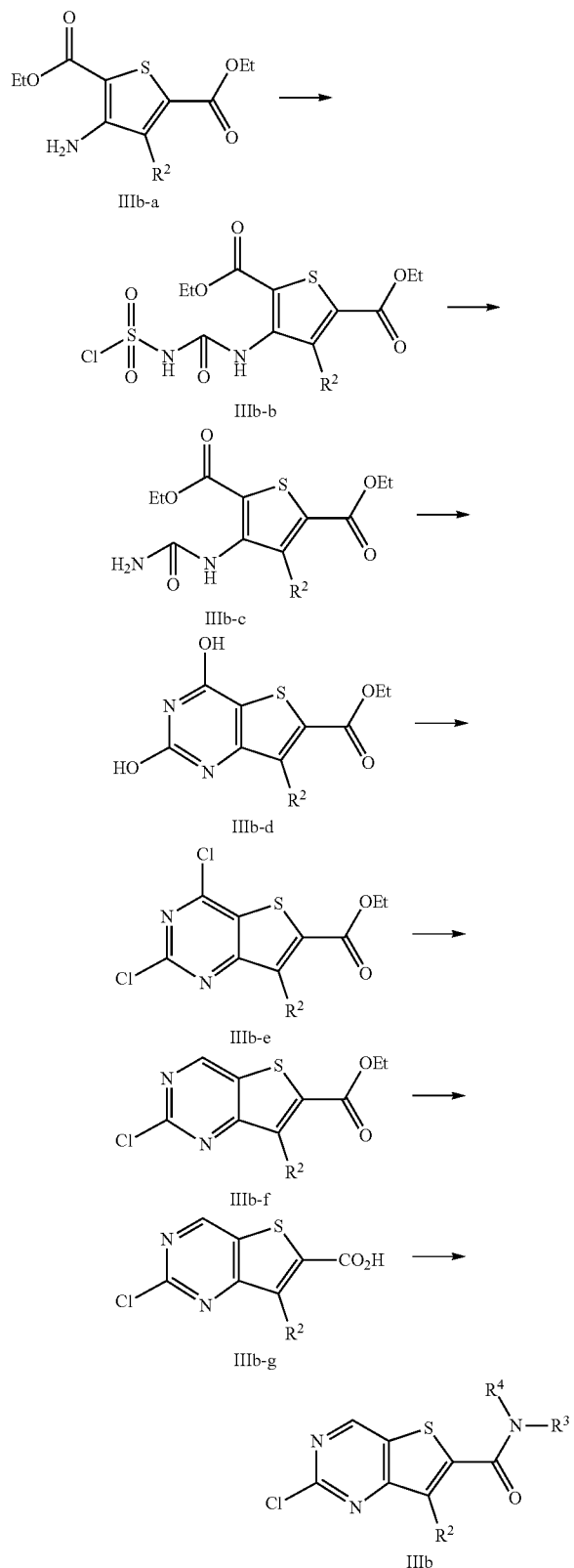

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1

7-cyclopentyl-N,N-dimethyl-2-((5-(4-(piperidin-4-yl)piperazin-1-yl)pyridin-2-yl)amino)thieno[3,2-d]pyrimidine-6-carboxamide (1)

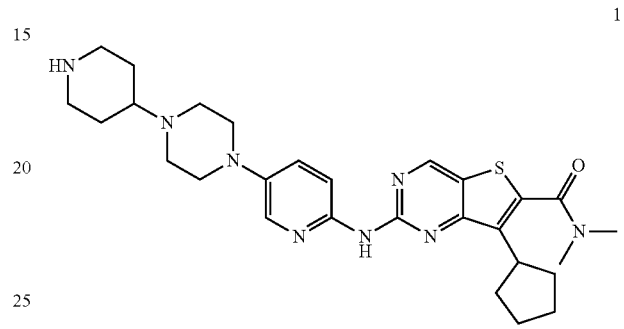

7-cyclopentyl-N,N-dimethyl-2-((5-(piperazin-1-yl-pyridin-2-yl)amino)thieno[3,2-d]pyrimidine-6-carboxamide (1a)

7-cyclopentyl-N,N-dimethyl-2-((5-(piperazin-1-yl)pyridin-2-yl)amino)thieno[3,2-d]pyrimidine-6-carboxamide (1a) was prepared according to the method described in WO 2015180642. MS-ESI (m/z): 452 [M+1]$^+$.

Tert-butyl 4-(4-(6-((7-cyclopentyl-6-(dimethylcarbamoyl) thieno[3,2-d]pyrimidin-2-yl)amino)pyridin-3-yl)piperazin-1-yl)piperidine-1-carboxylate (1b)

To a mixture of 7-cyclopentyl-N,N-dimethyl-2-((5-(piperazin-1-yl)pyridin-2-yl)amino)thieno[3,2-d]pyrimidine-6-carboxamide (1a) (1.0 g, 2.2 mmol) and tert-butyl 4-oxopiperidine-1-carboxylate (4.0 g, 19.9 mmol) in DCE (50 mL) were added HOAc (0.3 g) and NaBH(OAc)$_3$ (4.22 g, 19.9 mmol) at r.t. The mixture was stirred at 55° C. for 1 h. After cooling to r.t., the mixture was poured into saturated aqueous NaHCO$_3$ (300 mL), basified by saturated aqueous Na$_2$CO$_3$ and extracted with DCM (3×200 mL). The combined organic layer was dried over Na$_2$SO$_4$, concentrated and purified by s column chromatography on silica gel eluting with 5% MeOH in DCM to give tert-butyl 4-(4-(6-((7-cyclopentyl-6-(dimethylcarbamoyl)thieno[3,2-d]pyrimidin-2-yl)amino)pyridin-3-yl)piperazin-1-yl)piperidine-1-carboxylate (1b). MS-ESI (m/z): 635 [M+1]$^+$.

7-cyclopentyl-N,N-dimethyl-2-((5-(4-(piperidin-4-yl)piperazin-1-yl)pyridin-2-yl)amino)thieno[3,2-d]pyrimidine-6-carboxamide (1)

To a solution of tert-butyl 4-(4-(6-((7-cyclopentyl-6-(dimethylcarbamoyl)thieno-[3,2-d]pyrimidin-2-yl)amino)pyridin-3-yl)piperazin-1-yl)piperidine-1-carboxylate (1b) (1.3 g) in DCM (30 mL) was added TFA (14 mL) slowly at r.t. The mixture was stirred at r.t. for 30 min and concentrated. The residue was diluted with DCM (200 mL) and saturated aqueous NaHCO$_3$ (300 mL), extracted with 10% MeOH in DCM (3×200 mL). The combined organic layer was dried over Na$_2$SO$_4$ and concentrated to give 7-cyclopentyl-N,N-dimethyl-2-((5-(4-(piperidin-4-yl)piperazin-1-yl)pyridin-2-yl)amino)thieno[3,2-d]pyrimidine-6-carboxamide (1). MS-ESI (m/z): 535 [M+1]$^+$.

Example 2

7-cyclopentyl-2-((5-(4-(1-ethylpiperidin-4-yl)piperazin-1-yl)pyridin-2-yl)amino)-N,N-dimethylthieno[3,2-d]pyrimidine-6-carboxamide (2)

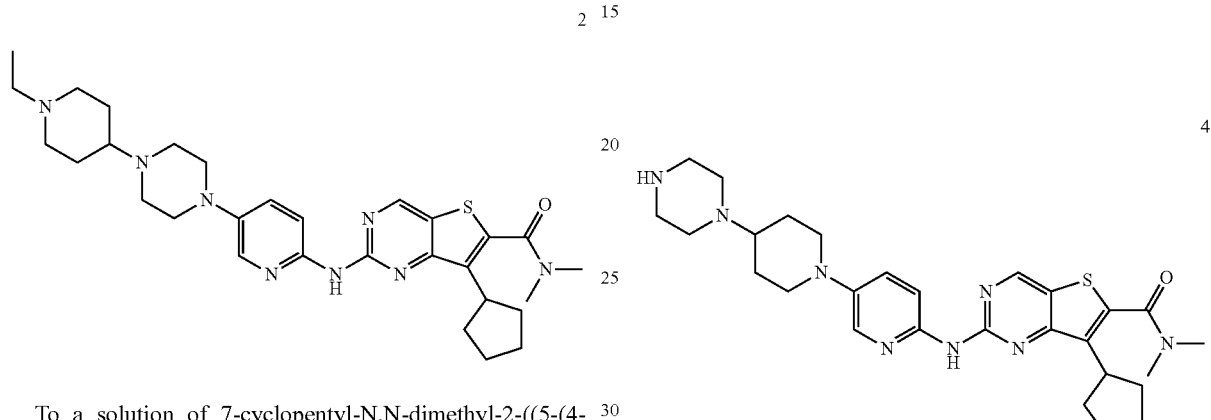

To a solution of 7-cyclopentyl-N,N-dimethyl-2-((5-(4-(piperidin-4-yl)piperazin-1-yl)pyridin-2-yl)amino)thieno[3,2-d]pyrimidine-6-carboxamide (1) (42 mg, 0.078 mmol) in DCM was added NaBH(OAc)$_3$ (50 mg, 0.235 mmol) followed by the addition of CH$_3$CHO (40% in water, 69 mg, 0.63 mmol). The mixture was stirred at r.t. for 30 min. The mixture was diluted with saturated aqueous NaHCO$_3$ (50 mL) and extracted with DCM (2×5 mL). The extracts were dried over Na$_2$SO$_4$. Solvents were evaporated under reduced pressure. The residue was purified by column chromatography on silica gel eluting with a gradient of 96:3:1 DCM/methanol/ammonia to give 7-cyclopentyl-2-((5-(4-(1-ethylpiperidin-4-yl)piperazin-1-yl)pyridin-2-yl)amino)-N,N-dimethylthieno[3,2-d]pyrimidine-6-carboxamide (2). MS-ESI (m/z): 563 [M+1]$^+$.

Example 3

7-cyclopentyl-N,N-dimethyl-2-((5-(4-(1-methylpiperidin-4-yl)piperazin-1-yl)pyridin-2-yl)amino)thieno[3,2-d]pyrimidine-6-carboxamide (3)

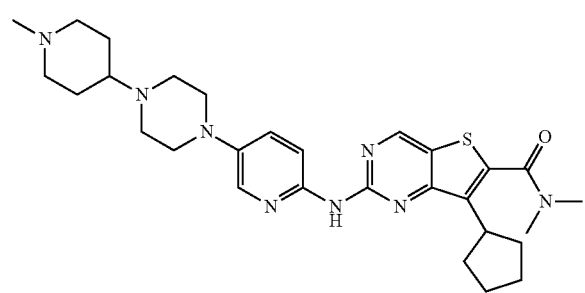

The title compound 7-cyclopentyl-N,N-dimethyl-2-((5-(4-(1-methylpiperidin-4-yl)piperazin-1-yl)pyridin-2-yl)amino)thieno[3,2-d]pyrimidine-6-carboxamide (3) was prepared according to the synthetic method of 2 by replacing CH$_3$CHO with CH$_2$O. MS-ESI (m/z): 549 [M+1]$^+$.

Example 4

7-cyclopentyl-N,N-dimethyl-2-((5-(4-(piperazin-1-yl)piperidin-1-yl)pyridin-2-yl)amino)thieno[3,2-d]pyrimidine-6-carboxamide (4)

Tert-butyl 4-(1-((benzyloxy)carbonyl)piperidin-4-yl)piperazine-1-carboxylate (4a)

To a mixture of tert-butyl piperazine-1-carboxylate (5.0 g, 26.9 mmol) and benzyl 4-oxopiperidine-1-carboxylate (19.1 g, 82.0 mmol) in DCE (150 mL) was added HOAc (3.0 g, 53.7 mmol) and NaBH(OAc)$_3$ (22.8 g, 107.5 mmol) at r.t. The mixture was stirred at 55° C. for 2 h. After cooling to r.t., the mixture was poured into saturated aqueous NaHCO$_3$ (1000 mL), basified by saturated aqueous Na$_2$CO$_3$ and extracted with DCM (3×200 mL). The combined organic layer was added to water (1000 mL) and acidified by aqueous HCl. The aqueous layer was basified by saturated aqueous Na$_2$CO$_3$ and extracted with DCM (3×200 mL). Solvents were evaporated under reduced pressure to give the title compound tert-butyl 4-(1-((benzyloxy)carbonyl)piperidin-4-yl)piperazine-1-carboxylate (4a). MS-ESI (m/z): 404 [M+1]$^+$.

Tert-butyl 4-(piperidin-4-yl)piperazine-1-carboxylate (4b)

To a solution of tert-butyl 4-(1-((benzyloxy)carbonyl)piperidin-4-yl)piperazine-1-carboxylate (4a) (6.9 g, 17 mmol) in EtOH (150 mL) was added Pd/C (3.4 g). The mixture was stirred under hydrogen at r.t. for 2 h and filtrated. The filtrate was concentrated under reduced pressure to give tert-butyl 4-(piperidin-4-yl)piperazine-1-carboxylate (4b). MS-ESI (m/z): 270 [M+1]$^+$.

Tert-butyl 4-(1-(6-nitropyridin-3-yl)piperidin-4-yl)piperazine-1-carboxylate (4c)

A mixture of tert-butyl 4-(piperidin-4-yl)piperazine-1-carboxylate (4b) (6.28 g, 23.3 mmol), 5-bromo-2-nitropyridine (4.74 g, 23.3 mmol), tetrabutylammonium iodide (0.52 g, 1.4 mmol) and $K_2CO_3$ (4.84 g, 35.0 mmol) in DMSO (100 mL) was stirred at 80° C. for 16 h. The mixture was cooled down, poured into ice water (500 mL) and extracted with DCM (3×200 mL). The extracts were dried over $Na_2SO_4$. Solvents were evaporated under reduced pressure. The residue was purified by column chromatography on silica gel eluting with 1% MeOH in DCM to give tert-butyl 4-(1-(6-nitropyridin-3-yl)piperidin-4-yl)piperazine-1-carboxylate (4c). MS-ESI (m/z): 392 $[M+1]^+$.

Tert-butyl 4-(1-(6-aminopyridin-3-yl)piperidin-4-yl)piperazine-1-carboxylate (4d)

To a solution of tert-butyl 4-(1-(6-nitropyridin-3-yl)piperidin-4-yl)piperazine-1-carboxylate (4c) (3.1 g, 7.93 mmol) in MeOH (150 mL) was added Pd/C (1.7 g). The mixture was stirred under hydrogen at r.t. for 2 h and filtrated. The filtrate was concentrated under reduced pressure to give tert-butyl 4-(1-(6-aminopyridin-3-yl)piperidin-4-yl)piperazine-1-carboxylate (4d). MS-ESI (m/z): 361 $[M+1]^+$.

7-cyclopentyl-N,N-dimethyl-2-(methylsulfonyl)thieno[3,2-d]pyrimidine-6-carboxamide (4e)

The title compound 7-cyclopentyl-N,N-dimethyl-2-(methylsulfonyl)thieno[3,2-d]pyrimidine-6-carboxamide (4e) was prepared according to the method described in WO 2015180642. MS-ESI (m/z): 354 $[M+1]^+$.

Tert-butyl 4-(1-(6-((7-cyclopentyl-6-(dimethylcarbamoyl)thieno[3,2-d]pyrimidin-2-yl)amino)pyridin-3-yl)piperidin-4-yl)piperazine-1-carboxylate (4f)

The title compound tert-butyl 4-(1-(6-((7-cyclopentyl-6-(dimethylcarbamoyl)-thieno[3,2-d]pyrimidin-2-yl)amino)pyridin-3-yl)piperidin-4-yl)piperazine-1-carboxylate (4f) was prepared according to the method described in WO 2015180642. MS-ESI (m/z): 635 $[M+1]^+$.

7-cyclopentyl-N,N-dimethyl-2-((5-(4-(piperazin-1-yl)piperidin-1-yl)pyridin-2-yl)amino)thieno[3,2-d]pyrimidine-6-carboxamide (4)

The title compound 7-cyclopentyl-N,N-dimethyl-2-((5-(4-(piperazin-1-yl)piperidin-1-yl)pyridin-2-yl)amino)thieno[3,2-d]pyrimidine-6-carboxamide (4) was prepared according to the synthetic method of Ic by replacing tert-butyl 4-(4-(6-((7-cyclopentyl-6-(dimethylcarbamoyl)thieno[3,2-d]pyrimidin-2-yl)amino)pyridin-3-yl)piperazin-1-yl)piperidine-1-carboxylate (1b) with tert-butyl 4-(1-(6-((7-cyclopentyl-6-(dimethylcarbamoyl)thieno[3,2-d]pyrimidin-2-yl)amino)pyridin-3-yl)piperidin-4-yl)piperazine-1-carboxylate (4f). MS-ESI (m/z): 535 $[M+1]^+$.

Example 5

7-cyclopentyl-N,N-dimethyl-2-((5-(4-(4-methylpiperazin-1-yl)piperidin-1-yl)pyridin-2-yl)amino)thieno[3,2-d]pyrimidine-6-carboxamide (5)

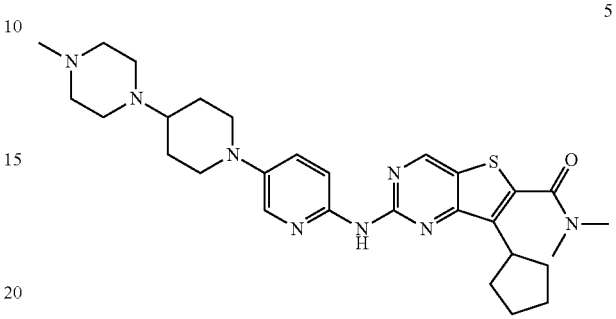

5

To a solution of 7-cyclopentyl-N,N-dimethyl-2-((5-(4-(piperazin-1-yl)piperidin-1-yl)pyridin-2-yl)amino)thieno[3,2-d]pyrimidine-6-carboxamide (4) (1.5 g, 2.8 mmol) in DCM (45 mL) was added $NaBH(OAc)_3$ (3.56 mg, 16.8 mmol) followed by $CH_2O$ (40% in water, 252 mg, 3.4 mmol). The mixture was stirred at r.t. for 30 min. The mixture was diluted with saturated aqueous $NaHCO_3$ (100 mL) and extracted with DCM (2×30 mL). The extracts were dried over $Na_2SO_4$. Solvents were evaporated under reduced pressure. The residue was purified by column chromatography on silica gel eluting with 96:3:1 DCM/methanol/ammonia to give 7-cyclopentyl-N,N-dimethyl-2-((5-(4-(4-methylpiperazin-1-yl)piperidin-1-yl)pyridin-2-yl)amino)thieno[3,2-d]pyrimidine-6-carboxamide (5). MS-ESI (m/z): 549 $[M+1]^+$.

Example 6

7-cyclopentyl-2-((5-(4-(4-ethylpiperazin-1-yl)piperidin-1-yl)pyridin-2-yl)amino)-N,N-dimethylthieno[3,2-d]pyrimidine-6-carboxamide (6)

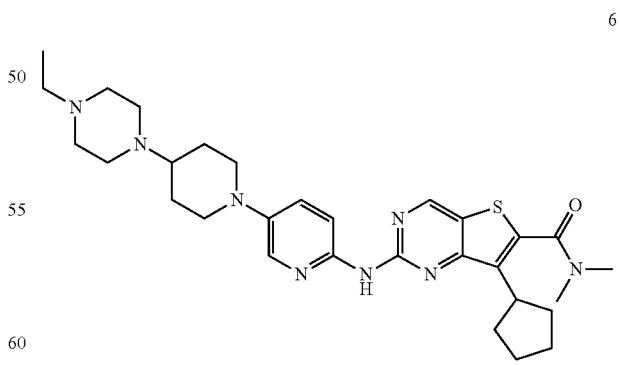

6

7-cyclopentyl-2-((5-(4-(4-ethylpiperazin-1-yl)piperidin-1-yl)pyridin-2-yl)amino)-N,N-dimethylthieno[3,2-d]pyrimidine-6-carboxamide (6) was prepared according to the synthetic method of 5 by replacing $CH_2O$ with $CH_3CHO$. MS-ESI (m/z): 563 $[M+1]^+$.

Example 7

7-cyclopentyl-N,N-dimethyl-2-((5-(4-morpholinopi-peridin-1-yl)pyridin-2-yl)amino)thieno[3,2-d]pyrimidine-6-carboxamide (7)

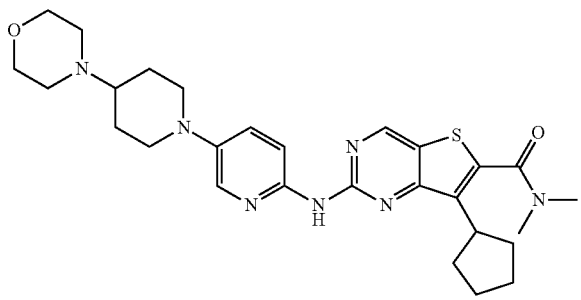

7

4-(piperidin-4-yl)morpholine (7a)

The title compound 4-(piperidin-4-yl)morpholine (7a) was prepared according to the method described in US2011/87021. MS-ESI (m/z): 171 [M+1]$^+$.

7-cyclopentyl-N,N-dimethyl-2-((5-(4-morpholinopi-peridin-1-yl)pyridin-2-yl)amino)thieno[3,2-d]pyrimidine-6-carboxamide (7)

The title compound 7-cyclopentyl-N,N-dimethyl-2-((5-(4-morpholinopiperidin-1-yl)pyridin-2-yl)amino)thieno[3,2-d]pyrimidine-6-carboxamide (7) was prepared according to the synthetic method of 4f by replacing tert-butyl 4-(piperidin-4-yl)piperazine-1-carboxylate (4b) with 4-(piperidin-4-yl)morpholine (7a). MS-ESI (m/z): 536 [M+1]$^+$.

Example 8

7-cyclopentyl-N,N-dimethyl-2-((5-(4-(4-(methyl-d$_3$)piperazin-1-yl)piperidin-1-yl)pyridin-2-yl)amino)thieno[3,2-d]pyrimidine-6-carboxamide (8)

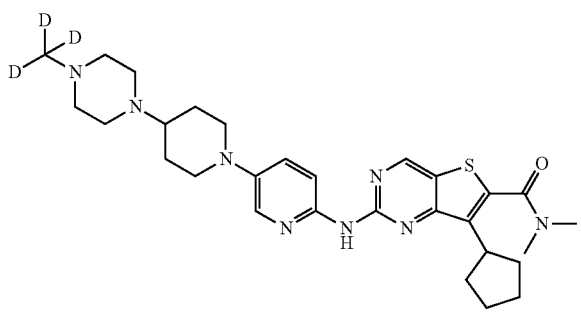

8

To a suspension of 7-cyclopentyl-N,N-dimethyl-2-((5-(4-(piperazin-1-yl)piperidin-1-yl)pyridin-2-yl)amino)thieno[3,2-d]pyrimidine-6-carboxamide (4) (3.05 g, 5.7 mmol) and K$_2$CO$_3$ (0.79 g, 5.7 mmol) in DMF (242 mL) was added iodomethane-d$_3$ (1.3 g, 9.0 mmol) portionwise. The mixture was stirred at r.t. for 17 h, and then saturated aqueous Na$_2$CO$_3$ (100 mL) was added, followed by the addition of (Boc)$_2$O (3.0 g, 13.8 mmol). The resulting mixture was stirred at r.t. for 1 h, and then water (1.8 L) was added. The resulting mixture was extracted with EtOAC (10×500 mL). The extracts were dried over Na$_2$SO$_4$ and concentrated under reduced pressure. The residue was purified by column chromatography on silica gel eluting with a gradient of 98:1:1 to 84:15:1 DCM/methanol/ammonia to give 7-cyclopentyl-N,N-dimethyl-2-((5-(4-(4-(methyl-d$_3$)piperazin-1-yl)piperidin-1-yl)pyridin-2-yl)amino)thieno[3,2-d]pyrimidine-6-carboxamide (8). MS-ESI (m/z): 552 [M+1]$^+$.

Reference Compound 1

7-cyclopentyl-N,N-dimethyl-2-(5-(4-methylpiperazin-1-yl)pyridin-2-ylamino)thieno[3,2-d]pyrimidine-6-carboxamide (Reference compound 1)

Reference compound 1 was disclosed and prepared following essentially the same procedures outlined on pages 39 and 40 of WO 2015/180642.

Cell Proliferation Assays

MTS testing kit was purchased from Promega. The DMEM, Fetal bovine serum and Penicillin-Streptomycin were purchased from Gibco. Dimethyl sulfoxide (DMSO) was purchased from Sigma.

To investigate whether a compound is able to inhibit the activity of CDK4/6 in cells, mechanism-based assays using BE2C (ATCC® number: CRL-2268) or JEKO-1 (ATCC® number: CRL-3006) cell were developed. In the assay, inhibition of CDK4/6 was detected by the inhibition of BE2C or JEKO-1 cell cells proliferation. BE2C or JEKO-1 cell cells were cultured in culture flasks to 40-80% confluence in DMEM plus 10% fetal bovine serum. Cells were collected and plated onto 96-well plates at desired cell density (BE2C: 3000 cells/well; JEKO-1: 30000 cells/well). Plates were incubated overnight at 37° C., with 5% CO$_2$ to adhere. Compounds were added to the plates, the final compound concentrations were 10000, 3333, 1111, 270, 123.5, 41.2, 13.7, 4.6 and 1.5 nM. Place plates at 37° C., with 5% CO$_2$ for 48 h. After removing the medium, 20 µl MTS/100 µl medium mixture solution were added to each well and incubate the plates for exactly 2 hours. Stop the reaction by adding 25 µl 10% SDS per well. Measure absorbance at 490 nm and 650 nm (reference wavelength). IC$_{50}$ was calculated using GraphPad Prism 5.0.

Select compounds prepared as described above were assayed according to the biological procedures described herein. The results were given in table 1. "+++" stands for IC$_{50}$ value between greater than about 10 nM to about 100 nM. "++" stands for IC$_{50}$ value between greater than about 100 nM to about 1 µM. "+" stands for IC$_{50}$ value greater than 1 µM.

TABLE 1

| Example | BE2C IC$_{50}$ (nM) | JEKO-1 IC$_{50}$ (nM) |
|---|---|---|
| 1 | / | ++ |
| 2 | +++ | ++ |
| 3 | +++ | ++ |
| 4 | ++ | / |
| 5 | +++ | +++ |
| 6 | +++ | +++ |
| 7 | +++ | / |

Tumor Growth Inhibition in COLO205 Xenograft Tumors

COLO205 cells were cultured with RPMI-1640 medium containing 10% fetal bovine serum (FBS) at 37° C. in 5% $CO^2$ incubator. Logarithmic growth phase cells were collected. COLO205 cells ($5\times10^6$ in 200 μL PBS) were implanted subcutaneously into the left flank region, and tumor growth was monitored. Tumor volume (V) was estimated from the length (l) and width (w) of the tumor using the following formula: $V=1/2\times l\times w^2$. Treatment started when average tumor size was 100-200 $mm^3$.

The dosage and dosage regimen were as shown table 2. Tumor volumes and mice weight were measured 2 to 3 times every week.

TABLE 2

| Group | Dosage (mg/kg) | Route | Number of Mice/ Group | Dosing Frenquence and Period |
|---|---|---|---|---|
| Vehicle | - - - | PO | 12 | QD × 14 days |
| Ribociclib (LEE011) | 60 | PO | 6 | QD × 14 days |
| Example 2 | 30 | PO | 6 | QD × 14 days |
| Example 5 | 60 | PO | 6 | QD × 14 days |
| Example 6 | 60 | PO | 6 | QD × 14 days |

Drug efficacy was assessed as Tumor Growth Inhibition (TGI) and T/C ratio. TGI was defined as $(1-T/C)\times100\%$, wherein T/C (%) presented the ratio of the change in mean tumor volume of the treated group and of the control group. Effects of Examples on COLO205 tumor volumes were shown in table 3.

TABLE 3

| Group | dosage (mg/kg) | T/C % | TGI % |
|---|---|---|---|
| Vehicle | - - - | | |
| Ribociclib (LEE011) | 60 | 25.6 | 74.40 |
| Example 2 | 30 | 0.88 | 99.12 |
| Example 5 | 60 | -2.31 | 102.31 |
| Example 6 | 60 | -2.97 | 102.97 |

Pharmacokinetic Properties in Dogs

Each test compounds was suspended in 0.5% methylcellulose (400 cP, w/v) in water.

Grouping male Beagle dogs was administered with test compound at a dose of 3 mg/kg by oral. After administering, blood samples were collected at time points of 0.25, 0.50, 1.0, 2.0, 4.0, 8.0 and 24.0 h. Standard curve was plotted based on concentrations of the samples in a suitable range, and the concentration of test compounds in plasma samples were determined by using LC-MS/MS. Pharmacokinetic parameters were calculated according to drug concentration-time curve using a non-compartmental method by Phoenix WinNonLin 6.3 software.

Results were given in table 4.

TABLE 4

| Example | Route | $T_{1/2}$ (h) | $C_{max}$ (ng/mL) | $AUC_{0-last}$ (ng·h/mL) | $AUC_{0-inf}$ (ng·h/mL) |
|---|---|---|---|---|---|
| 2 | p.o. | 26.0 | 127 | 2503 | 7010 |
| 5 | p.o. | 16.1 | 312 | 4663 | 7520 |
| 6 | p.o. | 13.2 | 404 | 5030 | 7343 |
| Reference Compound 1 | p.o. | 5.36 | 36 | 83 | 103 |

The results demonstrated that compounds disclosed herein have much longer $T_{1/2}$ and better AUCs than Reference Compound 1.

What is claimed is:

1. A compound of formula (II)

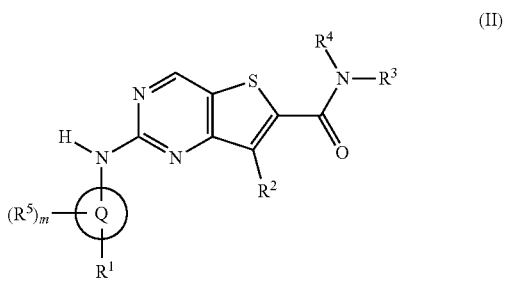

(II)

or a pharmaceutically acceptable salt thereof, wherein
Q is heteroaryl;
$R^1$ is heterocycle which is substituted with at least one substituent independently selected from $R^X$;
$R^2$ is $C_{3-10}$ cycloalkyl;
$R^3$ is selected from hydrogen, $C_{1-6}$ alkyl and $C_{3-10}$ cycloalkyl;
$R^4$ is selected from hydrogen, $C_{1-6}$ alkyl and $C_{3-10}$ cycloalkyl;
$R^5$ is independently selected from hydrogen and halogen;
each $R^X$ is independently selected from heterocyclyl, which is unsubstituted or substituted with at least one substituent independently selected from $R^Y$;
each $R^Y$ is independently selected from halogen, OH, CN, amino, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$ alkoxyalkyl, $C_{3-10}$ cycloalkoxy, $C_{1-6}$ alkylthio, $C_{3-10}$ cycloalkylthio, $C_{1-6}$ alkylamino, $C_{3-10}$ cycloalkylamino, di($C_{1-6}$ alkyl) amino;
m is selected from 0, 1, 2 and 3.

2. The compound of claim 1 or a pharmaceutically acceptable salt thereof, wherein Q is pyridinyl.

3. The compound of claim 2 or a pharmaceutically acceptable salt thereof, wherein Q is

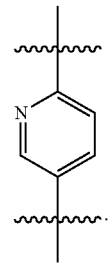 [SMILES: *c1ccc(*)nc1]

4. The compound of claim 1 or a pharmaceutically acceptable salt thereof, wherein $R^1$ is selected from piperazinyl and piperidinyl, which are independently substituted with at least one substituent independently selected from $R^X$.

5. The compound of claim 4 or a pharmaceutically acceptable salt thereof, wherein each $R^X$ is independently selected from piperazinyl, piperidinyl and morpholinyl, which is unsubstituted or substituted with at least one substituent independently selected from $R^Y$.

6. The compound of claim 5 or a pharmaceutically acceptable salt thereof, wherein each $R^Y$ is independently selected from $C_{1-6}$ alkyl.

7. The compound of claim 6 or a pharmaceutically acceptable salt thereof, wherein $R^Y$ is selected from methyl and ethyl.

8. The compound of claim 1 or a pharmaceutically acceptable salt thereof, wherein $R^2$ is selected from cyclopentyl and cyclohexyl.

9. The compound of claim 8 or a pharmaceutically acceptable salt thereof, wherein $R^2$ is cyclopentyl.

10. The compound of claim 1 or a pharmaceutically acceptable salt thereof, wherein $R^3$ and $R^4$ are independently hydrogen or $C_{1-6}$ alkyl.

11. The compound of claim 10 or a pharmaceutically acceptable salt thereof, wherein $R^3$ and $R^4$ are independently methyl.

12. The compound of claim 1 or a pharmaceutically acceptable salt thereof, wherein $R^5$ is hydrogen.

13. The compound of claim 1, selected from 7-cyclopentyl-N,N-dimethyl-2-((5-(4-(piperidin-4-yl)piperazin-1-yl)pyridin-2-yl)amino)thieno[3,2-d]pyrimidine-6-carboxamide, 7-cyclopentyl-2-((5-(4-(1-ethylpiperidin-4-yl)piperazin-1-yl)pyridin-2-yl)amino)-N,N-dimethylthieno[3,2-d]pyrimidine-6-carboxamide, 7-cyclopentyl-N,N-dimethyl-2-((5-(4-(1-methylpiperidin-4-yl)piperazin-1-yl)pyridin-2-yl)amino)thieno[3,2-d]pyrimidine-6-carboxamide, 7-cyclopentyl-N,N-dimethyl-2-((5-(4-(piperazin-1-yl)piperidin-1-yl)pyridin-2-yl)amino)thieno[3,2-d]pyrimidine-6-carboxamide, 7-cyclopentyl-N,N-dimethyl-2-((5-(4-(4-methylpiperazin-1-yl)piperidin-1-yl)pyridin-2-yl)amino)thieno[3,2-d]pyrimidine-6-carboxamide, 7-cyclopentyl-2-((5-(4-(4-ethylpiperazin-1-yl)piperidin-1-yl)pyridin-2-yl)amino)-N,N-dimethylthieno[3,2-d]pyrimidine-6-carboxamide, 7-cyclopentyl-N,N-dimethyl-2-((5-(4-morpholinopiperidin-1-yl)pyridin-2-yl)amino)thieno[3,2-d]pyrimidine-6-carboxamide, 7-cyclopentyl-N,N-dimethyl-2-((5-(4-(4-(methyl-$d_3$)piperazin-1-yl)piperidin-1-yl)pyridin-2-yl)amino)thieno[3,2-d]pyrimidine-6-carboxamide, and pharmaceutically acceptable salts thereof.

14. A pharmaceutical composition, comprising a compound of claim 1, or a pharmaceutically acceptable salt thereof, and at least one pharmaceutically acceptable carrier.

15. A method of treating a cancerous hyperproliferative disorder, comprising administering to a subject in need of such treatment an effective amount of a compound of claim 1, or a pharmaceutically acceptable salt thereof, or of at least one pharmaceutical composition thereof, wherein treatment refers to alleviating, abating or ameliorating a disease or condition, ameliorating the underlying metabolic causes of symptoms, relieving the disease or condition, causing regression of the disease or condition or relieving a condition caused by the disease or condition.

16. The compound of claim 1 or a pharmaceutically acceptable salt thereof, wherein $R^1$ is heterocycle which is substituted with one, two, three, or four substituents, independently selected from $R^X$.

17. The compound of claim 1 or a pharmaceutically acceptable salt thereof, wherein each $R^X$ is independently selected from heterocyclyl, which is substituted with one, two, three, or four substituents, independently selected from $R^Y$.

* * * * *